United States Patent
Hsu

(10) Patent No.: US 6,673,624 B2
(45) Date of Patent: Jan. 6, 2004

(54) METHOD AND DEVICE FOR DIAGNOSING DISEASE PATTERNS IN TRADITIONAL CHINESE MEDICINE

(76) Inventor: Ching-Hsiang Hsu, No. 2, Yue-Der Road, Taichung (TW)

( * ) Notice: Subject to any disclaimer, the term of this patent is extended or adjusted under 35 U.S.C. 154(b) by 0 days.

(21) Appl. No.: 09/834,296

(22) Filed: Apr. 12, 2001

(65) Prior Publication Data

US 2002/0098590 A1 Jul. 25, 2002

Related U.S. Application Data

(60) Provisional application No. 60/196,399, filed on Apr. 12, 2000.

(51) Int. Cl.$^7$ ................................................ G01N 33/00
(52) U.S. Cl. ........................................................ 436/86
(58) Field of Search ........................................... 436/86

(56) References Cited

PUBLICATIONS

Chen et al. "Activity of succinate dehydrogenase in hepatic cells of rat models of metabolic diseases (excess heat syndrome and deficiency heat syndrome in traditional Chinese medicine)", Beijing Zhongyiyao Daxue Xuebao (2000), 23(5), 48–49 (Abstract).*

Jin et al. "The contents of plasma norepinephrine and epinephrine in patients with five types of Gan syndromes in TCM and its significance for diagnosis", Hunan Yike Daxue Xuebao (1997), 22(1), 29–32 (Abstract).*

Kao et al. : "Effects of xiao–qing–long–tang (XQLT) on bronchoconstriction and airway eosinophil infiltration in ovalbumin–sensitized guinea pigs: In vivo and in vitro studies", : Allergy (Copenhagen, Denmark) (2001), 56(12), 1164–1171 (Abstract).*

Li et al. "The Chinese herbal medicine formula MSSM–002 suppresses allergic airway hyperreactivity and modulates TH1/TH2 responses in a murine model of allergic asthma".*

Hirai et al. "The effect of natural drugs on eotaxin production", Kanpo to Men'eki Arerugi (1998), 12, 387–47 (Abstract).*

Lin et al. "The effect of TCM on airway in asthmatic guinea pig", Shanghai Yixue (1996), 19(11), 638–641 (Abstractt).*

Tanno et al. "Effect of Chinese herbal medicine on the growth and accumlation of basophilic cells" Kanpo to Men'eki Arerugi (1991), 5, 39–48 (Abstract).*

Yu et al. "Association Between Disease Patterns in Chinese Medicine and Serum ECP in Allergic Rhinitis", Chin. Med. Coll. J., 1999, v. 8, No. 1, pp. 19–26.*

* cited by examiner

Primary Examiner—Jill Warden
Assistant Examiner—Yelena Gakh
(74) Attorney, Agent, or Firm—Cohen, Pontani, Lieberman & Pavane

(57) ABSTRACT

The present invention provides a method of facilitating the diagnosis, monitoring and treatment of a human patient by measuring the ECP level in the patient's blood, and determining whether the patient is within the heat pattern group or the non-heat pattern group based on the measure ECP level.

4 Claims, 3 Drawing Sheets

BARS REPRESENT MEAN VALUES FOR EACH GROUP ± SEM

* INDICATES p<0.01

BARS REPRESENT MEAN VALUES FOR EACH GROUP ± SEM

* INDICATES p<0.01

METHOD AND DEVICE FOR DIAGNOSING DISEASE PATTERNS IN TRADITIONAL CHINESE MEDICINE

This application claims the benefit of Provisional Application No. 60/196,399, filed Apr, 12, 2000.

BACKGROUND OF THE INVENTION

1. Field of the Invention

The present invention relates to a method and device for diagnosing or identifying patterns of human pathological conditions defined according to the principles of Traditional Chinese Medicine. More particularly, the invention pertains to an application of objective data obtained using modern analytic technologies as a diagnostic means to the practice of Traditional Chinese Medicine. Such an application would substantially reduce subjectiveness and inconsistency often associated with the pattern identification methods originally employed by the ancient healing art.

2. Description of the Related Art

Traditional Chinese Medicine (thereinafter "TCM") has been in existence for several thousands of years and is based largely on accumulated human experience in fighting various diseases through the long history of Chinese civilization. Understandably, the development of TCM, including its diagnosis and treatment theories, did not benefit from modern science and technology and thus cannot be easily understood from the perspective of modern biology and medicine.

In TCM, human diseases are categorized by, first, the general patterns of imbalance of physiological conditions, i.e., pathological conditions and, then, by the specific organs affected by such imbalance. The most commonly used terms for general pathological patterns are: Heat, cold, excessive and lacking. These general conditions may affect one or more organs, such as heart, lung, spleen, liver, stomach, etc. It should be noted, however, that these references to organs do not have the same meanings in TCM as in modern medicine. For example, heart in TCM refers not only to the pumping object within one's chest but, more importantly, also refers to one's mind and spirit. Thus, anxiety or depression may be regarded as a heart disease in TCM. According to TCM, all diseases are caused by one or more of the general types of physiological imbalances and each type of imbalances has an identifiable pattern of clinical manifestations and requires a particular set of treatments for correction. Thus, to cure a disease, a doctor not only needs to treat the symptoms specific to the affected organ but also needs to treat the underlying general imbalance which, to some extent, is more important. Therefore, it is very important for a TCM doctor to correctly identify the underlying general disease patterns.

Traditionally, a TCM doctor relies on four types of examination to identify disease patterns and provide treatment accordingly: observation-inspection, listening-smelling, inquiry and palpation. Those types of examinations rely heavily on the doctor's subjective judgment and different diagnostic results are often obtained from different doctors examining the same subject. Therefore, it is highly desirable to have some objective means to help TCM doctors in disease pattern identification. Although, efforts have been made to link "yin-yang" to cellular levels of cAMP-cGMP, no one to applicants' knowledge has heretofore developed or suggested a practical use of objective biological data as a diagnostic means to be used in TCM. The present invention, by providing an association between a biochemical marker and a disease pattern of TCM, advances TCM into the modern era. It provides more objective and consistent identifications of disease patterns for better treatment results. It also provides a better understanding of TCM and makes it more acceptable to more people.

The methods of diagnosing and treating allergic asthma, for instance, have been very different according to TCM and western medicine. Although the incidence and severity of allergic asthma seem to be rising, western methods of treatment still stem from empirical and serendipitous findings rather than from a scientific approach (Barnes, P. J. A new approach to the treatment of asthma. *N Engl J Med.* 321:1517–27, 1989). At present, allergic asthma may be treated using different approaches. Drug treatment that aimed at controlling the symptoms resulting from the release of mediators by effector cells seems in short-term studies to be effective, with a low frequency of adverse effects. Long-term oral steroid therapy is associated with multiple debilitating effects, such as growth delay, osteoporosis, and adrenal suppression. As a result, steroid agents are often attempted in patients.

The alternative view in the treatment of asthma is TCM. One of the most comprehensive anti-asthma TCM clinical trial, a multi-center, double-blind and placebo-controlled study, was reported in Taiwan (Hsieh, K.H. Evaluation of efficacy of traditional Chinese medicines in the treatment of childhood bronchial asthma: clinical trial, immunological tests and animal study. *Pediatr Allergy Immunol.* 7:130–140, 1996). The results showed that the TCM treatments were beneficial to the patients, while many other clinical indicators did not show statistically significant differences between treatment and placebo. One of the reasons is probably the essence of TCM diagnosis was not clearly included in the trial.

TCM diagnosis depends on the doctor's sense of the patient's organs to acquire clinical information, then to analyze, generalize and infer the patient's condition without resorting to any apparatus. The reason why a doctor can diagnose internal pathological changes merely by observation and analysis of external signs when he is unable to inspect directly the pathological changes in the interior is that the human body is an organic whole, with its parts intimately and inseparably connected with each other by the channels and collateral. So pathological changes inside of the human body are inevitably shown outwardly as abnormalities in complexion, spirit, picture of the tongue and the pulse (Hsu H.Y., and W.G. Peacher. General Diagnosis in Chinese Herbal Medicine. In: *Chinese Herb Medicine and Therapy*. New Canaan: Oriental Healing arts Institute of the United States, 1982, pp. 19–26). Therefore, only by accurate differentiation of syndromes can we work out effective treatments according to the condition of the disease. The treatment of asthma in TCM is based on the differentiation of "heat" zheng according to the patient's outward manifestations. However, there is little published work to provide objective evidences for the nature of zheng.

Heat syndrome indicates functional hyperreactivity of the body, arising from affection of pathogenic heat, or fire transformation from disorder of the emotions, and hyperreactivity of yang due to deficiency of yin. Heat syndrome is typically shown as dryness of the mouth, slight thirst, red tip and borders of the tongue, floating and rapid pulse, preference for drinking, scanty dark urine, constipation (Kuwaki, T. Introduction to Chinese Herbal Therapy. In: *Chinese Herbal Therapy*. Long Beach: Oriental Healing Arts Institute. 1990, pp. 21–38). In our clinic, we found asthmatic patients presented their symptoms in varying pattern.

Oriental medical doctors will treat these patients in different ways based on the results of differentiation of syndromes. Patients who exhibit yellowish mucoid sputum, thirst, onset closely associated with heat, reddened tongue with yellow greasy fur, slippery and rapid pulse will be treated by removing heat-phlegm and facilitating the flow of the lung-qi to relieve asthma. In our studies, patients with blood-shot eyes, aversion to heat, thirst with desire for drinking, constipation, dark scanty urine and red tongue with yellow fur were classified into "heat" zheng. On the other hand, patients without these presentations were classified into "non-heat" zheng.

The present invention found that asthmatic patients with typical heat "zheng" presentation always had higher ECP serum level. Therefore we believe that ECP should be one of the pathogenic pathway of heat zheng presentation.

Eosinophils play an important role in the pathogenesis of bronchial asthma. Eosinophil cationic protein (ECP) as a cytotoxic performed mediator stored in eosinophil granules and released under various in vitro and vivo conditions (Koller, D.Y, Y. Herouy, M. Gotz, E. Hagel, R. Urbanek, and I. Eichler. Clinical value of monitoring eosinophil activity in asthma. *Arch Dis Child.* 73:413–417, 1995; Remes, S., M. Korppi, K. Remes, K. Savolainen, I. Mononen, and J. Pekkanen. Serum eosinophil cationic protein and eosinophil protein X in childhood asthma. *Pediatr Pulmonol.* 25:167–174, 1998). A correlation has been documented between the activity of the eosinophils in the lungs and the level of ECP in serum. In addition, ECP is a sensitive marker for monitoring of the disease activity in asthma and offer a useful tool for estimating treatment efficacy (Niimi, A., R. Amitani, K. Suzuki, E. Tanaka, T. Murayama, and F. Kuze. Serum eosinophil cationic protein as a marker of eosinophilic inflammation in asthma. *Clin Exp Allergy* 28:233–240, 1998). Studies have indicated a relation between level of serum ECP and activity and severity in asthma. Therefore measurement of ECP indicates the activity of activated eosinophils. Until the present invention, however, there has been no correlation of the patient's ECP serum level to the patient's classification as being within "heat" zheng or "non-heat" zheng.

SUMMARY OF THE INVENTION

In accordance with the present invention, a disease pattern categorized according to TCM can be linked to one or more biochemical markers. By measuring those markers, a TCM doctor can better identify TCM disease patterns, more objectively and consistently, especially in patients suffering from allergic disorders, such as rhinitis, asthma, and eczema. Further, according to the present invention, analytical kits for the measurement can be manufactured, making the identification more economical and convenient.

As one of the embodiments of the present invention, the serum level of ECP (serum eosinophil cationic protein) was used to correctly identify patients with the Heat Pattern of allergic rhinitis, which is traditionally identified by so-called "heat syndrome" or "heat zheng": dryness of the mouth, slight thirst, red tip and rim of the tongue, floating and rapid pulse, scanty dark urine and constipation. The serum ECP level can be objectively and quantitatively measured by using one of various biochemical assays, such as radioimmunoassay or fluorescence enzyme-linked immunosorbent assay. Such a measurement is in contrast to the traditional pattern identification method, as aforementioned, which is more subjective and qualitative and must be determined by experienced clinical TCM doctors. In addition, ECP assay kits can be manufactured in large scale to further reduced the costs and permit the assay to be performed by ordinary lab technicians.

Therefore, one of the objectives of the present invention is to provide a diagnostic method for identifying TCM disease patterns more objectively and consistently. This objective is achieved by providing a direct link between a disease pattern and one or more biochemical markers which can be objectively measured.

Another objective of the present invention is to provide a more convenient and more economic way for clinical disease pattern identification. This objective is achieved by providing standardized assay kits manufactured in large scale.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the claims.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings, wherein like reference characters denote similar elements throughout the several views.

DETAILED DESCRIPTION OF THE PRESENTLY PREFERRED EMBODIMENTS

Figure 1:
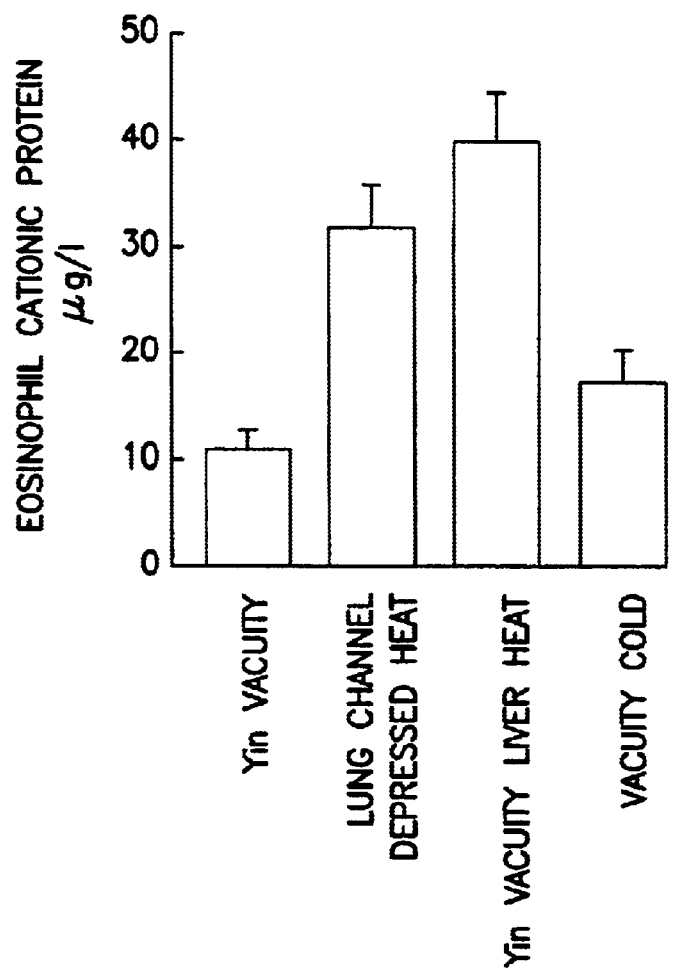
FIG. 1 depicts the different serum ECP levels measured in allergic rhinitis patients with different patterns of general pathological conditions.

The titer of allergen-specific IgE is important in the pathogenesis of Type 1 hypersensitivity, like asthma. High IgE level usually cause airways hyperactivity and inflammation. However, we cannot find any correlation between heat zheng and the titer of high specific IgE. The number of peripheral circulating eosinphils also showed no relation with "heat" zheng presentation.

We demonstrated that asthmatic patients with "heat syndrome" also have higher serum ECP level. Our disclosure showed that elevation of serum ECP level in a patient suffering allergic asthma is usually a good indication that this patient belong to the heat-pattern group classified by TCM diagnostic criteria. To the best of our knowledge this is the first time a biochemical marker has been identified to be closely linked to the TCM diagnostic classification. By using a biochemical assay to detect the serum ECP of a patient, one can determine the "heat" or "non-heat" pattern of a patient, either at the beginning of a treatment course for choosing the proper treatment, or during a TCM treatment for monitoring the progress of a treatment. Thus a diagnostic device or kit based on this principle would be useful, and can be used to replace the more subjective traditional diagnostic methods of looking into the patient's "heat" syndrome.

In this particular embodiment of the present invention, the serum ECP level is used to identify allergic rhinitis and asthma patients with the Heat Pattern of general pathological conditions, because the Heat Pattern patients, whether suffering from allergic rhinitis or asthma, have significantly elevated serum ECP levels. The portion of the embodiment concerning allergic rhinitis patients is published in The China Medical College Journal 8(1) 19–16, 1999, entitled "The association between disease patterns in Chinese Medicine and serum ECP in allergic rhinitis." The publication is attached hereto and its content is incorporated herein by reference in its entirety.

Related Theories of Traditional Chinese Medicine

In tradition Chinese medicine (TCM), the imbalance of yin and yang is one of the basic pathogenesis of a disease. Preponderance of yang leads to hyperfunction of the organism and heat syndrome. TCM analyzes the relevant information, signs and symptoms collected through the four methods of diagnosis (observation, listening and smelling, inquiring, pulse feeling and palpation) in determining the corresponding therapeutic method. Such symptoms as high fever, flushed face, blood-shot eyes, aversion to heat, thirst with desire for drinking, constipation, dark scanty urine and red tongue with yellow fur are regarded as "heat" syndrome (zheng). Treatment with heat-reducing agents is applicable to heat syndrome, i.e., patients with Heat Pattern. Therefore, the definition of "heat" zheng plays key roles in the diagnosis and treatment of diseases. Though this definition of heat syndrome is important in the treatment of disease in the TCM, the essence of "heat" zheng was not clear in terms of modem science.

Significance of ECP in Allergic Disorders

Eosinophilic cationic protein (ECP) is one of the several cytotoxic proteins secreted by the eosinphils. In allergic rhinitis and asthma, two inflammatory diseases affecting 20% and 6–9% of the population in Taiwan, respectively, the eosinophils become activated and are major constituents of the inflammation in the airways. It has been suggested that the extensive epithelial damage seen in asthmatic patients is caused by eosinophil granule proteins. The presence of activated eosinophils in those patients can be shown by measuring ECP in serum. Furthermore, the effects of anti-inflammatory treatment can be followed by measuring serum ECP. However, the relationship between ECP and "heat" zheng or the Heat Pattern is unclear. The present invention discloses that, at least for allergic rhinitis and asthma, patients with heat zheng have higher serum ECP level.

Patients Selection 69 patients of allergic rhinitis were recruited and, after examination according to TCM diagnostic criteria, were divided into four Pattern identification categories. See table 1. These four categories are yin vacuity (Yin Xu), lung channel depressed heat (Fei Jing Yu Re), yin vacuity liver heat (Yin Xu Gan Re), and vacuity cold (Xu Han). Patients with lung channel depressed heat and yin vacuity liver heat were gathered as the "heat"-pattern group. "Non-heat"-pattern patients were grouped by yin vacuity and vacuity cold categories. "Heat"-pattern patients were grouped because of the indications of blood-shot eyes, aversion to heat, while thirst with desire for drinking, constipation, dark scanty urine and red tongue with yellow fur typically related to "heat" Zheng.

Another group of 166 patients with asthma were recruited for the study of the present invention. See Table 2. Those asthmatic patients, from age 5 to 35, suffered with episodes of dyspnea, cough, and wheezing which require intermittent or frequent bronchodilator treatment, met the American Thoracic Society's criteria for asthma. They had a forced expiratory volume per second (FEV1) of 50% or greater of the normal level, and showed a reversibility of at least 15% of the baseline following an inhalation of a bronchodilator. The total serum IgE titer was in the 95 percentile or above of their respective age groups. All patients had a value of the cardinal features greater than 0.35 kU/L, which is defined as the threshold point for a positive result of the CAP system.

Definition of "Heat" Zheng

For both allergic rhinitis patients and asthmatic patients with three of the following criteria: blood-shot eyes, aversion to heat, thirst with desire for drinking, constipation, dark scanty urine and red tongue with yellow fur were diagnosed "heat" Zheng. The confirmation of "heat" zheng was performed by the same oriental medical doctor (Dr. M.C. Yu).

Immunoassays for Specific IgE and Total IgE Antibodies

Specific IgE antibodies to house dust mite allergens were measured by quantitative fluoroimmunoassays with the CAP System FEIA (Kabi Pharmacia Diagnostics, Uppsala, Sweden). This system is a complete modular system for in vitro testing of specific IgE response to allergens. Immuno-CAPs are specially designed cellulose sponges with covalently bound allergen. The allergens used were D. P. In each assay a standard curve was constructed with known IgE antibody standard solutions ranging from 0.35 to 50 kU/L IgE antibody calibrated against the WHO Second International Reference Preparation 75/502 human IgE. After incubation of the specific ImmunoCAP with the serum sample for 30 minutes, the ImmunoCAP sponge was washed and a rabbit β-galactosidase anti-IgE complex was added; the bound complex on the ImmunoCAP was then incubated for 10 minutes with a developing agent (4-methylumbelliferyl-β-D-galactoside). After final elution of the ImmunoCAPs, the fluorescence of the eluate was measured. Both negative sera and serial dilutions of known positive sera were run in parallel with each assay. A value greater than 0.35 kU/L is defined as a positive CAP System result. Total IgE was measured by microparticle enzyme immunoassay testing with the IMX system (Abbott Diagnostics, Chicago, Ill.) according to the manufacturer's instructions. Total IgE can also be measured by radioimmunoassay. The results are expressed in International Unit per liter. The interassay and intraassay coefficients of variation were less than 10%.

Measurement of Eosinophils and ECP

The absolute count of peripheral eosinophils was obtained by conventional methods. Serum levels of eosinophfil cationic protein (ECP) were assessed by radioimmunoassay (Pharmacia, Uppsala, Sweden) according to the method used by Venge et al. with a sensitivity of 2 µg/L. Radioactivity detected was inversely proportional to the amount of ECP. Values were expressed as means±SEM.

Statistical Analysis

A. Allergic Rhinitis

Student's t test and analysis of variance were used to determine significance of mean differences between groups, as appropriate. A p value of less than 0.05 was considered statistically significant.

B. Asthma

Mann-Whitney U-test was used to determine significance of median difference between groups, as appropriate. A p value of less than 0.05 was considered statistically significant.

Results

A. Allergic Rhinitis

Figure 2:
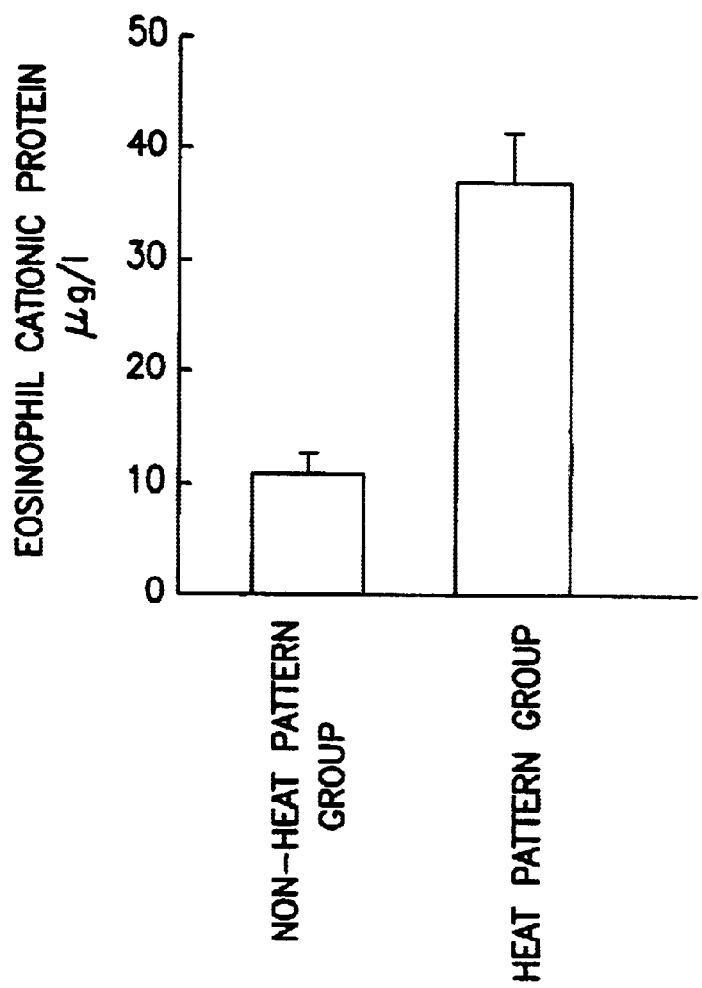
FIG. 2 depicts the comparison of the serum ECP levels in allergic rhinitis patients of "Heat" Pattern and in allergic rhinitis patients of "Non-Heat" Pattern.

With reference to FIG. 1, the serum ECP levels among the four categories were: yin vacuity, 10.51+/1.59 µg/l; lung channel depressed heat, 31.87+/−6.11 μg/l; yin vacuity liver heat, 39.17+/−6.25 μg/l; and vacuity cold, 16.21+/−3.96 μg/l. Statistically, when the ECP level of the heat-pattern group was compared with that of the non heat pattern group, as shown in FIG. 2, very significant difference was found ($P<0.001$, by Student t test).

The serum IgE values among the four categories were: yin vacuity, 503.0+/−159.3 IU/ml; lung channel depressed heat, 779.6+/−268.3 IU/ml; yin vacuity liver heat, 742.7+/−128.7 IU/ml; and vacuity cold, 514.5+/−241.9 IU/ml. Statistically, when the IgE level of the heat-pattern group was compared with that of the non heat pattern group, no significant difference was found.

The serum eosinophil counts among the four categories were: yin vacuity, 119.6+/−104.4 per μl; lung channel depressed heat, 92.3+/−97.6 per μl; yin vacuity liver heat, 140.8+/−156.6 per μl; and vacuity cold, 79.8+/−82.7 per μl. Statistically, when the eosinophil counts of the heat-pattern group was compared with that of the non heat pattern group, no significant difference was found.

We have generally found that patients with ECP levels of more than 15 microgram per liter indicate active allergic inflammation or disease. Patients with ECP levels more than 20 microgram per liter are one within the heat pattern group.

B. Asthma

Figure 3:
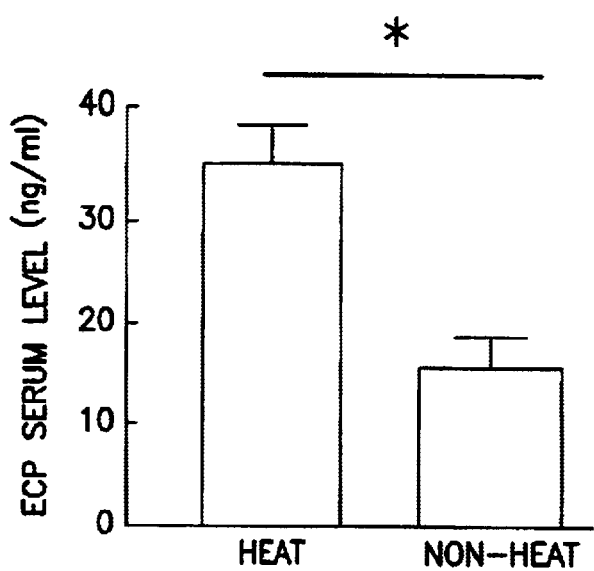
FIG. 3 depicts the comparison of the serum ECP levels in asthmatic patients of "Heat" Pattern and in asthmatic patients of "Non-Heat" Pattern.

The same relationship between ECP and the Heat Pattern in allergic rhinitis patients was also found in asthma patients studied, as shown in FIG. 3. The serum ECP level of asthmatic patients with the Heat Pattern was found to be 34.3±4, in contrast with 15.3±3 found in non-Heat pattern asthmatic patients. This result indicated that there was a Z-fold increase in ECP serum level in asthmatic patient with "heat"-pattern. There was a significant difference between the two groups ($p<0.01$). Similarly, in the asthmatic patients, no correlation was found between the Heat Pattern and the total serum IgE level or the eosinophil count in the peripheral blood.

While there have been shown, described and pointed out the features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention.

All publications cited herein are incorporated by reference in their entirety.

TABLE 1

Base-line characteristics of the four TCM diagnostic groups of allergic rhinitis patients

| Characteristic | Yin Vacuity (n = 8) | Lung channel Depressed heat (n = 23) | Yin vacuity liver heat (n = 30) | Vacuity cold (n = 8) |
|---|---|---|---|---|
| Male/Female (male %) | 3/5 (38%) | 12/11 (52%) | 20/10 (67%) | 4/4 (50%) |
| Had allergy family history | 3 | 17 | 24 | 4 |

TABLE 1-continued

Base-line characteristics of the four TCM diagnostic groups of allergic rhinitis patients

| Characteristic | Yin Vacuity (n = 8) | Lung channel Depressed heat (n = 23) | Yin vacuity liver heat (n = 30) | Vacuity cold (n = 8) |
|---|---|---|---|---|
| Had asthma history | 5 | 13 | 14 | 1 |
| Total IgE | 503.0 ± 159.3 | 779.6 ± 258.3 | 742.7 ± 128.7 | 514.3 ± 241.9 |
| Eosinophil # | 119.6 ± 104.4 | 92.3 ± 97.4 | 140.8 ± 156.6 | 89.8 ± 82.7 |

TABLE 2

Base-line characteristics of the "Heat" and "Non-heat" groups of asthmatic patients

| Characteristic | Heat (n = 123) | Non-heat (n = 43) |
|---|---|---|
| Male/Female (male %) | 88/45 (75%) | 28/15 (70%) |
| Age (yr) | 12.9 ± 5 | 13.9 ± 6 |
| Weight (kg) | 36.3 ± 15.9 | 30.2 ± 11.7 |
| Height (cm) | 126.7 ± 22.5 | 130.4 ± 19.2 |

What I claim is:

1. A method for facilitating the diagnosis of a human patient suffering from an allergic disorder, comprising measuring the eosinophil cationic protein level in the blood of the patient; and determining whether the patient is within the heat or non-heat pattern groups defined in terms of Traditional Chinese Medicine based on the measured eosinophil cationic protein level.

2. The method of claim 1 wherein the allergic disorder is selected from the group consisting of rhinitis, asthma, and eczema.

3. A method for facilitating the diagnosis of a human patient suffering from an allergic disorder, comprising measuring the eosinophil cationic protein level in the blood of the patient; and determining whether the patient is within the heat or non-heat pattern groups defined in terms of Traditional Chinese Medicine based on the measured eosinophil cationic protein level, wherein the human patient is within the heat pattern group if the eosinophil cationic protein level is 20 microgram per liter or more.

4. The method of claim 3 wherein the allergic disorder is selected from the group consisting of rhinitis, asthma, and eczema.

* * * * *